United States Patent [19]
Fowler et al.

[11] Patent Number: 5,537,035
[45] Date of Patent: Jul. 16, 1996

[54] APPARATUS AND METHOD FOR DETECTING ANOMALIES IN FERROUS PIPE STRUCTURES

[75] Inventors: J. Thomas Fowler, Marblehead, Mass.; Steven S. Carroll, South Hampton, N.H.

[73] Assignee: Gas Research Institute, Chicago, Ill.

[21] Appl. No.: 241,152

[22] Filed: May 10, 1994

[51] Int. Cl.$^6$ ............... G01N 27/82; G01N 27/72; G01R 27/72

[52] U.S. Cl. ............... 324/220; 324/232; 324/242; 324/247

[58] Field of Search ............... 324/219–221, 324/232, 244, 247, 260, 262, 242

[56] References Cited

U.S. PATENT DOCUMENTS

| | | | |
|---|---|---|---|
| 3,443,211 | 5/1969 | Wood et al. | 324/220 X |
| 3,460,028 | 8/1969 | Beaver et al. | 324/220 |
| 3,593,122 | 7/1971 | Barton | 324/220 |
| 4,105,972 | 8/1978 | Smith | 324/220 |
| 4,439,730 | 3/1984 | Kauffman | 324/232 |
| 4,442,403 | 4/1984 | Pohler | 324/220 |
| 4,480,225 | 10/1984 | Nance et al. | 324/220 |
| 4,594,549 | 6/1986 | Smith et al. | 324/232 |
| 4,649,343 | 3/1987 | Birchak et al. | 324/220 |
| 4,742,298 | 5/1988 | Ando et al. | 324/220 |
| 4,855,676 | 8/1989 | Cecco et al. | 324/220 |
| 5,258,755 | 11/1993 | Kuckes | 324/244 X |
| 5,293,117 | 3/1994 | Hwang | 324/220 |

FOREIGN PATENT DOCUMENTS

| | | |
|---|---|---|
| 0266103 | 5/1988 | European Pat. Off. . |
| 2143331 | 2/1985 | United Kingdom . |

*Primary Examiner*—Sandra L. O'Shea
*Assistant Examiner*—Jay M. Patidar
*Attorney, Agent, or Firm*—Dick and Harris

[57] ABSTRACT

An apparatus and method for detecting anomalies in ferrous pipe structures is presented. A sensor having one or more sensor shoe members is placed in the interior of a ferrous pipe structure to be inspected. Each sensor shoe member has one or more magnetic field generating apparatus, with a three-axis fluxgate magnetometer for detecting magnetic fields in the region of the ferrous pipe structure adjacent to which the sensor shoe member is placed. Any magnetic fields in the pipe structure, whether imposed externally, or remnant, which are detected, are sensed and resolved into components in three mutually orthogonal directions for enhanced accuracy.

3 Claims, 1 Drawing Sheet

U.S. Patent          Jul. 16, 1996          5,537,035
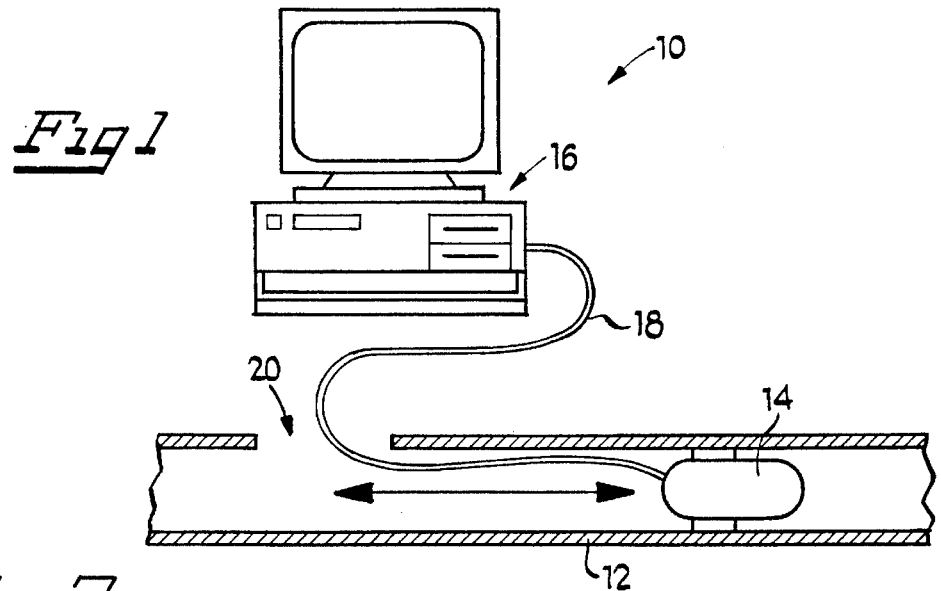
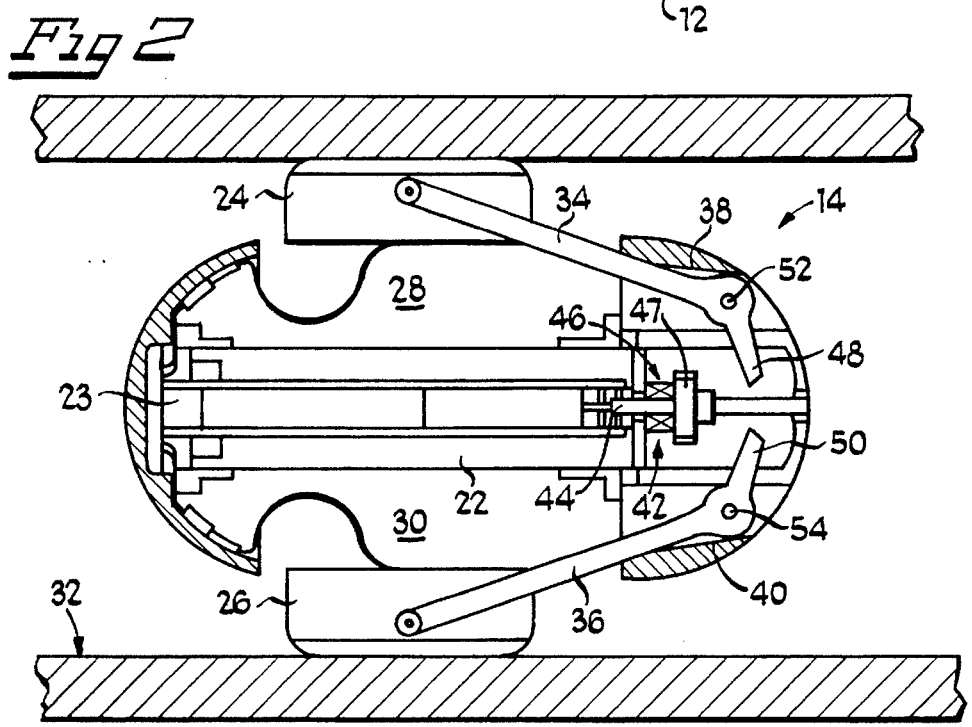
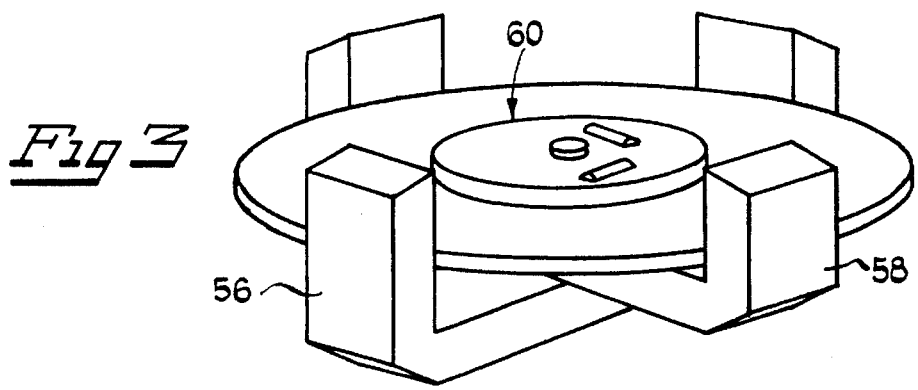

APPARATUS AND METHOD FOR DETECTING ANOMALIES IN FERROUS PIPE STRUCTURES

BACKGROUND OF THE INVENTION

1. Field of the Invention

The present invention relates to the field of apparatus and method for detecting anomalies in ferrous pipe structures, such as natural gas or oil pipelines, through the use of magnetic sensors which are passed along the interior of the pipe structures.

2. The Prior Art

Piping systems, such as natural gas or oil piping systems, need to be inspected, during and after construction, and periodically after use has begun, for the purposes of detecting defects or points of failure or leakage, or in some cases, predicting such points of failure or leakage. Since such pipelines typically are buried or submerged, it has become necessary to develop a means for inspecting such pipe structures using preprogrammed robotic or remotely operated or teleoperated devices.

It is known, for example, that in ferrous pipe structures, such as are used for natural gas or petroleum, the pipe will have a residual or remnant magnetic field associated with it, which can be detected and measured by appropriate electromagnetic sensors placed next to or against the pipe structure. It is also known that by placing magnetic field sources next to such pipe structures, a portion of the magnetic flux from the sources can be forced to travel through the pipe structure. When sensors are activated to seek the imposed field(s) passing through a pipe structure, if the particular local section of pipe is without welds, flaws or other anomalies, then the imposed fields will not be detected. If, however, the local section of pipe has welds, cracks, or other flaws or anomalies, then the imposed field will "leak" from the anomaly and be detected by the sensors, when the leakage field is compared to the profile of the residual or remnant field detected and measured for the same local section of pipe.

Numerous examples of anomaly detection devices, using magnetic field generators and magnetic field sensors, exist in the prior art, including such devices as are disclosed in Beaver et al., U.S. Pat. Nos. 3,460,028; Barton, 3,593,122; Smith, 4,105,972; Birchak et al., 4,649,343; Ando et al., 4,742,298; and Cecco et al., 4,855,676.

The Beaver et al. '028 reference shows an anomaly detector having a single axially oriented magnetic field generating apparatus centrally arranged within the sensor rig. Annular brushes positioned fore and aft of a plurality of magnetic field sensor "sledges" on the sensor rig convey the magnetic field into and out of the pipe structure, such that the magnetic flux lines are parallel to the longitudinal axis of the pipe structure. The "sledges" are held in spring-biased relation against the interior surface of the pipe structure, as the sensor rig moves along the interior of the pipe structure.

The apparatus of the Barton '122 patent likewise employs fore and aft magnetic pole pieces to establish an axially extending magnetic flux path, with sensor "shoes" positioned axially between the pole pieces. An additional pole piece, positioned aft of the paired pole pieces, and having brush parts inclined relative to the interior surface of the pipe structure acts to strengthen the residual magnetic field in the pipe structure. The residual fields detected are compared to the readings taken when the pipe structure has the active magnetic field imposed upon it. The discrepancies in the two sets of readings indicates the presence of anomalies, which may be welds, or actual flaws in the pipe structure.

The Smith '972 patent shows a pipeline inspection vehicle having a plurality of sensor heads arranged in a circle about the vehicle, and held in place against the interior surface of the pipe structure by an annular, spring-biased structure. Each individual sensor head may have magnetic field generating apparatus therein, as well as magnetic field sensing apparatus.

The Birchak et al. '343 patent describes an inspection system for use in small bore tubes, in which a scanner body has two annular magnetic cores, arranged perpendicular to one another, inside a hollow core of the scanner body. An array of magnetic field sensors are arranged circumferentially around the scanner body. The field generated by the two magnetic cores, simultaneously, may be manipulated by phase shifting and amplitude variations, so as to shift the direction of the field, even to producing a helical magnetic flux, or to swing the flux through nearly 180° to expose an anomaly to magnetic flux directed normal to it.

The apparatus of the Ando et al. '298 patent employs an axially extending primary magnetic coil, and a plurality of circumferentially extending secondary coils positioned radially outwardly of the primary coil. The secondary coils do not impose a magnetic field, but rather sense the axial component of the magnetic flux generated by the primary coil, in the form of a voltage imposed on the secondary coil. The sensed component changes in the presence of a flaw positioned between the poles of the primary coil.

The Cecco et al. '676 reference shows an apparatus for inspection of a pipe, having a sensor member configured to produce both axially extending and radially extending magnetic fields, positioned along the length of the sensor member. The Cecco et al. reference describes that both fields are of such strength as to obtain very high levels of saturation in the pipe structure.

The present invention is particularly directed to inspection systems for ferrous pipe structures, which are particularly suited to small bore pipe structures, such as the piping systems for natural gas distribution, the pipes of which typically have a nominal four-inch interior diameter. Commonly, prior art defect detection systems, which have typically been configured for much larger diameter pipes, have relied upon detection techniques involving the complete saturation of the pipe structure by the generated magnetic fields. Such saturation involves substantial power consumption by electromagnets, or the use of large, typically heavy, permanent magnets.

To provide logistical support, such as power cables and transformers or sufficiently powerful and durable portable power supplies for electromagnets, and/or conveyance mechanisms for the sensors for saturation-type detector devices, in the confined environment of a small-bore detector device, is a difficult task. It is desirable, therefore, to provide a way of avoiding the logistical difficulties presented by saturation-type detector systems.

Typically, prior art systems simply measured the magnitudes of the residual/remnant fields and the leakage fields. However, such magnetic fields have other quantifiable and measurable characteristics, such as the phase of the field. It would be desirable to provide an apparatus which can take a wider, more detailed variety of field measurements, rather than taking simple magnitude measurements, as such would enable the use of more compact, smaller powered and lighter sensor apparatus, as would be needed and appropriate for smaller diameter pipe structures.

In addition, prior art devices, such as those mentioned, use as the magnetometers, devices such as Hall Effect sensors, which may lack sufficient sensitivity to detect flaws, in low-power applications, and devices such as coil magnetometers, which require the sensor unit to be in fairly rapid motion in order to obtain readings at all. It would be desirable therefore, to provide a pipeline sensor apparatus capable of high sensitivity even in low power applications, and which can take readings at rest.

SUMMARY OF THE INVENTION

The present invention is directed, in part, to an apparatus for detecting anomalies in a ferrous pipe structure. The apparatus comprises sensor means, operably configured for positioning within and movement along an interior of the ferrous pipe structure. Associated with the sensor means are means to impose one or more magnetic fields into the structure; means to detect magnetic fields emanating from the ferrous pipe structure, whether due to remnant induction in the ferrous pipe structure or to magnetic fields imposed by the means to impose magnetic fields, wherein the means to detect magnetic fields in the ferrous pipe structure are operably configured to detect components of magnetic fields emanating from the pipe structure, in at least three orthogonal directions, relative to the sensor means; and means to generate data signals corresponding to the magnetic fields detected by the means to detect magnetic fields.

In addition, control means for receiving and processing the data signals generated by the sensor means, and for converting the data signals into information from which a user may determine the presence and characteristics of anomalies in the ferrous pipe structure are provided, as well as means for communicating the data signals generated by the sensor means to the control means and means for propelling the sensor means along the interior of the ferrous pipe structure.

In a preferred embodiment of the invention, the sensor means comprises a sensor support frame and at least one sensor shoe member operably configured to be placed sufficiently adjacent to an interior surface of the ferrous pipe structure so as to enable imposition of a magnetic field generated within the sensor shoe member onto the ferrous pipe structure and to enable detection, within the sensor shoe member, of magnetic fields in the ferrous pipe structure. The sensor support frame additionally includes means for operably positioning the at least one sensor shoe member adjacent to the interior surface of the ferrous pipe structure.

In a preferred embodiment, the means for imposing magnetic fields comprises at least two magnetic members operably disposed in the at least one sensor shoe member, to generate at least two magnetic fields in at least two orthogonal directions relative to the sensor means and impose the magnetic fields onto the ferrous pipe structure.

The means to detect magnetic fields in the ferrous pipe structure comprises a three-axis fluxgate magnetometer operably disposed in the at least one sensor shoe member, so as to detect components of magnetic fields emanating from the ferrous pipe structure, in at least three mutually orthogonal directions.

The means for communicating the data signals generated by the sensor means to the control means comprises a hardwire connection from the sensor means to the control means. Alternatively, the means for communicating the data signals generated by the sensor means to the control means may be telemetry means operably associated with the sensor means and the control means for transmitting the data signals from the sensor means to the control means without a hardwire connection therebetween, or means for recording the data signals generated by the sensor means, for playback into the control means after retrieval of the sensor means from the interior of the ferrous pipe structure.

The preferred embodiment of the invention also comprises a method for detecting anomalies in a ferrous pipe structure, of the kind employing an apparatus including a sensor to be positioned in and propelled along the interior of the ferrous pipe structure, wherein the sensor includes at least one sensor shoe member. The method includes the steps of a) placing the at least one sensor shoe member within the interior of the ferrous pipe structure at a desired location to be inspected; b) measuring any present remnant magnetic field within the ferrous pipe structure, as a combination of at least three components extending along mutually orthogonal directions; c) imposing a first magnetic field onto the ferrous pipe structure with a first magnetic field source and simultaneously measuring any magnetic field emanating from the ferrous pipe structure, as a combination of at least three components extending along mutually orthogonal directions; d) imposing a second magnetic field of reversed polarity onto the ferrous pipe structure with the first magnetic field source and simultaneously measuring any magnetic field emanating from the ferrous pipe structure, as a combination of at least three components extending along mutually orthogonal directions; and e) comparing the remnant magnetic field measured with the magnetic fields measured after imposition of the first and second magnetic fields to yield data representative of anomalies in the ferrous pipe structure at the desired location.

In an alternative preferred embodiment, the method also includes the steps of: f) imposing a third magnetic field onto the ferrous pipe structure with a second magnetic field source positioned orthogonally to the first magnetic field source, within the sensor and simultaneously measuring any magnetic field emanating from the ferrous pipe structure, as a combination of at least three components extending along mutually orthogonal directions; g) imposing a fourth magnetic field of reversed polarity onto the ferrous pipe structure with the second magnetic field source and simultaneously measuring any magnetic field emanating from the ferrous pipe structure, as a combination of at least three components extending along mutually orthogonal directions; and h) comparing the remnant magnetic field with the magnetic fields measured after imposition of the third and fourth magnetic fields to yield data representative of anomalies in the ferrous pipe structure at the desired location.

BRIEF DESCRIPTION OF THE DRAWINGS

FIG. 1 is a schematic view of the apparatus for detecting anomalies in a pipe structure according to the present invention;

FIG. 2 is a side elevation, partially in section, of a sensor apparatus according to the present invention, shown with the sensor shoe members deployed against the inner surface of a pipe structure; and FIG. 3 is a semi-schematic view of the magnetic field generators and magnetic field sensors arranged in each sensor shoe member, according to the present invention.

BEST MODE FOR CARRYING-OUT THE INVENTION

While the present invention is susceptible of embodiment in many different forms, there is shown in the drawings and will be described herein in detail, one specific embodiment, with the understanding that the present disclosure is to be considered as an exemplification of the principles of the invention, and is not intended to limit the invention to the embodiment illustrated.

FIG. 1 shows in schematic form, apparatus 10 for detecting anomalies in ferrous pipe structures, such as pipe structure 12. Apparatus 10 includes sensor 14, control computer 16, and a means for communication between sensor 14 and control computer 16. Although such communication means is shown in FIG. 1 as being represented by a hardwire connection 18, other types of communication, such as by a telemetry device or a data storage device (either of which may be of otherwise known design and can thus be generally designated by reference numeral 23) in sensor 14, among others, for later playback of recorded data and downloading into control computer 16, are also contemplated.

In addition, sensor 14 must be provided with some form of propulsion back and forth along the interior of pipe structure 12. Sensor 14 may be moved by a push rod (not shown), examples of which are well known in the art, which may be externally controlled through breach 20 in pipe structure 12. Alternatively, sensor 14 may be attached to or constructed as part of a self-propelled robot crawler (not shown), examples of which are already known in the art.

Sensor 14, shown in FIG. 2, includes sensor support frame 22 and sensor shoe members 24, 26. Sensor 14 may include a greater or lesser number of sensor shoe members, and preferably should have as many as possible arranged about the circumference of sensor 14, to provide as great a coverage of the surface of the pipe structure 12 as possible. Sensor shoe members 24, 26 are configured to be deployed from positions in pockets 28, 30, immediately adjacent to sensor support frame 22, to be held in a resiliently biased manner against the inner surface 32 of pipe structure 12.

Deployment and maintenance of sensor shoe members 24, 26 against inner surface 32 can be obtained by pivotably supporting sensor shoe members 24, 26 on arms 34, 36. Arms 34, 36 may be suitably biased, such as by springs 38, 40, so as to tend to press sensor shoe members 24, 26 against inner surface 32. To retract arms 34, 36, a ballscrew mechanism 42, of any suitable known configuration, may be provided, such that upon actuation and rotation of the screw 44, for example by an electric motor, a ballnut 46 will be propelled axially in the direction of wings 48, 50 of arms 34, 36. Ballnut 46 will drive an actuator member 47 against wings 48, 50, causing arms 34, 36 to pivot about axes 52, 54, against the bias of springs 38, 40, thus withdrawing sensor shoe members 24, 26 back into pockets 28, 30. The deployment and retraction of sensor shoe members 24, 26 may also be used when sensor 14 must pass obstacles or restrictions in pipe structure 12.

Sensor support frame 22 of sensor 14 also provides space for the placement and protection of various electronic circuitry, as further discussed hereinafter.

Within each sensor shoe member, such as sensor shoe member 24, is provided a combination of two magnetic field sources and a set of magnetic field sensing devices, such as are shown semischematically in FIG. 3. First magnetic field coil 56 is arranged perpendicular to second magnetic field coil 58, such that the fields generated by the first and second coils likewise will be normal to one another.

In an alternative embodiment, each sensor shoe member 24 might be provided with only one magnetic coil, or, indeed one coil only may be provided, extending either axially or transversely in sensor 14. It is contemplated that sensor readings may be taken using only one field generating coil, which could still indicate the presence of anomalies, albeit with less detail than by using the apparatus in the illustrated preferred embodiment.

A three-axis fluxgate-type magnetometer 60 is arranged substantially centrally in the yoke of the two-axis magnetic flux source containing first magnetic field coil 56 and second magnetic field coil 58. Appropriate circuitry for driving and actuating the field coils 56 and 58, for driving the magnetometer 60, and for taking the analog signals generated by magnetometer 60 and converting them into digital data signals for processing by control computer 16, are located in sensor support frame 22.

The procedure for inspection of a particular local section of pipe structure is as follows. The sensor 14 is placed in the desired local section to be inspected. Sensor shoe members 24, 26 are in their deployed positions, against inner surface 32 of pipe structure 12. With both field coils unpowered, magnetometer 60 measures the residual/remnant field in the local region of the pipe structure, taking measurements, which are resolved into vectors having components in three orthogonal axes, for example, an X-axis, concentric with the longitudinal axis of the pipe structure, and Y- and Z-axes being normal both to the X-axis and each other.

One of the field coils, for example, first magnetic field coil 56, which may be suitably arranged so as to project a magnetic field having a flux pattern generally parallel to the longitudinal axis of the pipe structure 12, is then powered up, and the fluxgate magnetometer 60 again takes readings, in the manner previously described. The power to coil 56 is then cut off and reversed, so as to generate a magnetic field of reversed polarity, with magnetometer 60 again taking readings. If more than one field generating coil is used, such as coil 58, coil 56 is then shut off, and coil 58 is powered up, measurements are taken, the power to coil 58 is reversed, and a final set of measurements are taken.

The readings from the fluxgate magnetometer, as previously mentioned, which typically are in the form of analog electrical signals, may be converted to digital data signals by an onboard analog-to-digital circuitry of known configuration, carried in central support portion 22 of sensor 14. This digital data may then be stored in an onboard recording device, such as digital memory, or may be immediately transmitted, via hardwire, or telemetry, if appropriate transmission circuitry is provided, to control computer 16. Once all the pertinent data for a particular inspection location have been recorded or transmitted, the sensor 14 may then be propelled to the next desired inspection location along pipe structure 12.

The data obtained by the inspection procedure may be processed through a comparison of the residual/remnant field readings at a particular inspection location, with the readings taken when field coils 56, 58 are utilized. Where defects or other anomalies occur, the superposition of the imposed fields upon the residual/remnant field can lead to known particular results which can suggest upon the type of anomaly which is found. For example, in general, anomalies such as welds or hard spots (which are more likely sites of possible future failure) may have different residual magnetism and a comparison of the residual and imposed fields is different than similar readings taken in the vicinity of, for example, cold worked regions, where the pipe may have been accidentally or intentionally bent, or dented, during installation.

The taking of measurements of residual and imposed fields, along three coordinate axes, in particular, using 3-axis fluxgate magnetometers, facilitates the comparison of such readings, and can provide an even more detailed understanding of the configuration and orientation of such anomalies, in a manner not practical with the use of simple saturation measurement techniques, and Hall Effect or coil-type magnetometers. Accordingly, such a measurement, and, in turn the present apparatus itself, alleviates the need for the bulkier, and more powerful magnets used with such systems.

The comparison of the residual and induced fields is performed, at each inspection location, by making the residual field measurements and resolving them along the three coordinate axes as described, and treating those readings as the X-, Y- and Z-axis components of a vector. If an anomaly is located, it will be seen as a different magnetic field having a different position and orientation, and thus a different vector, than the residual field. Using known trigonometric and/or various modeling techniques, among others (such as digital signal processing techniques) the coordinates of that new vector, and thus the positioning of the anomaly, can be determined.

As can be understood from the disclosure, the magnetometers carried by sensor 14 are capable of detecting magnetic fields emanating from the pipe structure 12, whether the magnetic fields are imposed upon the pipe structure 12 from the magnets in sensor shoe members 26, or from some other source. For example, for the detection of certain specific kinds of hard-to-detect defects, a more powerful imposed magnetic field may be called for. Since the space available for powerful, permanent, or powered, magnets is restricted in narrow pipe applications, an alternate method of imposing a magnetic field is required.

It has been found that a suitable magnetic field may be imposed in the pipe structure, if an electrical current is longitudinally passed through the pipe structure itself, such as by connecting distant ends of the section to the poles of an electrical generator. The magnetic flux thus created would be directed circumferentially about the pipe structure, and could substitute for, or augment, the fields imposed by the electromagnets carried onboard the sensor, in the procedure. The fields imposed could be varied, depending on the polarity of the current through the pipe, whether the current is alternating or direct, constant or pulsed, in a particular phase, and so on. It is believed this technique lends itself to detection of anomalies on the outer surfaces of pipe structures.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An apparatus for detecting anomalies in a ferrous pipe structure, comprising:

sensor means operably configured for positioning within and movement along an interior of the ferrous pipe structure, the sensor means including means for imposing one or more magnetic fields into the ferrous pipe structure operably associated with the sensor means, means operably disposed proximate the means for imposing one or more magnetic fields, for detecting magnetic fields emanating from the ferrous pipe structure whether due to remnant induction in the ferrous pipe structure or to magnetic fields imposed by the means to impose magnetic fields, the means to detect magnetic fields in the ferrous pipe structure being operably configured to detect components of the magnetic fields in the ferrous pipe structure, in at least three orthogonal directions, relative to the sensor means, means to generate data signals representative of at least one characteristic of the magnetic fields detected by the means to detect magnetic fields;

control means for receiving and processing the data signals generated by the sensor means, and for converting the data signals into information from which a user may determine the presence and characteristics of anomalies in the ferrous pipe structure;

means for communicating the data signals generated by the sensor means to the control means; and means for propelling the sensor means along the interior of the ferrous pipe structure;

the sensor means including a sensor support frame;

at least one sensor shoe member, operably configured to be placed sufficiently adjacent to an interior surface of the ferrous pipe structure so as to enable imposition of a magnetic field generated within the sensor shoe member onto the ferrous pipe structure and to enable detection, within the sensor shoe member, of magnetic fields in the ferrous pipe structure, and means for operably positioning the at least one sensor shoe member adjacent to the interior surface of the ferrous pipe structure, the means for imposing one or more magnetic fields further including at least two magnetic members, operably disposed in the at least one sensor shoe member, so as to selectively generate at least two magnetic fields at angles to one another, and selectively impose the magnetic fields into the pipe structure.

2. A method for detecting anomalies in a ferrous pipe structure, of the kind employing an apparatus, including a sensor to be positioned in and propelled along the interior of the ferrous pipe structure, wherein the sensor includes at least one sensor shoe member; the method for detecting anomalies in a ferrous pipe structure comprising the steps of:

placing the at least one sensor shoe member within the interior of the ferrous pipe structure at a desired location to be inspected;

measuring any present remnant magnetic field within the ferrous pipe structure, as a combination of at least three components extending along mutually orthogonal directions, with a magnetic field detecting apparatus disposed on the sensor shoe member;

imposing a first magnetic field onto the ferrous pipe structure with a first magnetic field source disposed on the sensor shoe member and simultaneously measuring any magnetic field emanating from the ferrous pipe structure, as a combination of at least three components extending along mutually orthogonal directions;

ceasing the imposition of the first magnetic field;

imposing a second magnetic field of reversed polarity onto the ferrous pipe structure with the first magnetic field source and simultaneously measuring any magnetic field emanating from the ferrous pipe structure, as a combination of at least three components extending along mutually orthogonal directions;

comparing the remnant magnetic field measured with the magnetic fields measured after imposition of the first and second magnetic fields to yield data representative of at least one characteristic of a resultant magnetic field evidencing the presence of one or more anomalies in the ferrous pipe structure at the desired location.

3. The method for detecting anomalies in a ferrous pipe structure, according to claim 2, further comprising the steps of:

imposing a third magnetic field onto the ferrous pipe structure with a second magnetic field source positioned orthogonally to the first magnetic field source, on the sensor shoe member and simultaneously measuring any magnetic field emanating from the ferrous pipe structure, as a combination of at least three components extending along mutually orthogonal directions;

ceasing the imposition of the third magnetic field;

imposing a fourth magnetic field of reversed polarity onto a ferrous pipe structure with the second magnetic field source and simultaneously measuring any magnetic field emanating from the ferrous pipe structure, as a combination of at least three components extending along mutually orthogonal directions.

* * * * *